United States Patent
Qvist

(10) Patent No.: US 7,387,995 B2
(45) Date of Patent: *Jun. 17, 2008

(54) METHOD FOR ATTACHING TWO SURFACES TO EACH OTHER USING A BIOADHESIVE POLYPHENOLIC PROTEIN AND PERIODATE IONS

(75) Inventor: Magnus Qvist, Alingsås (SE)

(73) Assignee: Stryker Development LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/637,011

(22) Filed: Dec. 12, 2006

(65) Prior Publication Data

US 2007/0160744 A1 Jul. 12, 2007

Related U.S. Application Data

(62) Division of application No. 10/509,401, filed as application No. PCT/SE03/00492 on Mar. 25, 2003, now Pat. No. 7,186,690.

(60) Provisional application No. 60/374,129, filed on Apr. 22, 2002.

(30) Foreign Application Priority Data

Mar. 26, 2002 (SE) .................... 0200924

(51) Int. Cl.
*A61K 38/00* (2006.01)
*C07K 14/00* (2006.01)
(52) U.S. Cl. .......................... 514/2; 530/350
(58) Field of Classification Search ...................... None
See application file for complete search history.

(56) References Cited

U.S. PATENT DOCUMENTS

| | | | |
|---|---|---|---|
| 5,015,677 A | 5/1991 | Benedict et al. | |
| 5,242,808 A | 9/1993 | Maugh et al. | |
| 5,410,023 A | 4/1995 | Burzio | |
| 5,817,470 A | 10/1998 | Burzio et al. | |
| 6,506,577 B1 | 1/2003 | Deming et al. | |

FOREIGN PATENT DOCUMENTS

WO   WO 9933499 A2   7/1999

WO   WO 0144401 A1   6/2001

OTHER PUBLICATIONS

Miaoer Yu and Timothy J. Deming, Synthetic Polypeptide Mimics of Marine Adhesives, Macromolecules 1998, vol. 31, 4739-4745.
Rzepecki et al; "Dopa Proteins: Versatile Varnishes and Adhesives From Marine Fauna"; College of Marine Studies, University of Delaware, Lewes, DE, 1998, pp. 118-148.
Saby et al.; "Mytilus Edulis Adhesive Protein (Map) as an Enzyme Immobilization Matrix in the Fabrication of Enzyme-Based Electrodes"; Electroanalysis, 1998, vol. 10, No. 17, pp. 1193-1199.
Fischer et al., "In vitro cytotoxicity testing of polycations: influence of polymer structure on cell viability and hemolysis" Biomaterials 24 (2003) 1121-1131.
Morgan et al., "Biochemical characterization of polycation-induced cytotoxicity to human vascular endothelial cells", Journal of cell Science 94 (1989) 553-559.
Abstract of King et al., "Improvement of the biocompatibility of alginate/poly-L-lysine/alginate microcapsules by the use of epimerized alginate as a coating", 3 Biomed Matr Res A 2003, 64, 533-9.
Abstract of Strand et al., "Poly-L-Lysine induces fibrosis on alginate microcapsules via the induction of cytokines", Cell Transplant 2001, 10, 263-75.
Abstract Needham et al., "Endothelial functinoal responses and increased vascular permeability induced by polycations", Lab Invest 1988 538-548.

*Primary Examiner*—Robert B Mondesi
(74) *Attorney, Agent, or Firm*—Nixon & Vanderhye P.C.

(57) ABSTRACT

The present invention pertains to a method for attaching two surfaces to each other or coating a surface by providing a bioadhesive composition consisting of an aqueous solution of a bioadhesive polyphenolic protein derived from a byssus-forming mussel, and mixing said bioadhesive composition with a preparation comprising non-enzymatic oxidising periodate ions so that the concentration of periodate ions is at least 1.80 mmol/g in the final composition before applying the mixture to at least one of two surfaces to be attached to each other or coated or applying said composition and said periodate ions without any specific order, to at least one of two surfaces to be attached to each other or the surface to be coated, thereby mixing the bioadhesive composition and the periodate ions. The surfaces are then joined (if necessary) and left for sufficiently long time for curing to occur. The invention can be provided as a kit of parts comprising the MAP-solution, a preparation comprising the periodate ions and optionally a device to apply the compositions of the invention to surfaces that are to be attached to each other or coated.

6 Claims, No Drawings

METHOD FOR ATTACHING TWO SURFACES TO EACH OTHER USING A BIOADHESIVE POLYPHENOLIC PROTEIN AND PERIODATE IONS

The present application is a divisional of U.S. application Ser. No. 10/509,401, filed Sep. 24, 2004 now U.S. Pat. No. 7,186,690, which is a national stage application of International Application PCT/SE03/00492, filed Mar. 25, 2003, designating the United States of America, which claims the benefit of Swedish Patent Application No. 0200924-9, filed Mar. 26, 2002, and U.S. Provisional Patent Application No. 60/374,129, filed Apr. 22, 2002, the entire contents of each of which is hereby incorporated by reference in this application.

The present invention pertains to a method for attaching two surfaces to each other or coating a surface, comprising the steps of providing a bioadhesive composition consisting of a bioadhesive polyphenolic protein derived from a byssus-forming mussel, mixing the bioadhesive protein with a high amount of non-enzymatic oxidising periodate ions before or simultaneously as applying the composition to the surfaces which are to be attached to each other or the surface to be coated. The surfaces are then joined and left for a sufficiently long time to allow curing to occur alternatively the surface coated by the composition is left for a sufficiently long time to allow curing to occur. The invention can be provided as a kit of parts comprising the bioadhesive protein solution and a preparation comprising a periodate salt.

BACKGROUND OF THE INVENTION

Attachment of different structures is crucial in a wide variety of processes. However, this is frequently associated with problems of different nature depending on what structures are to be attached.

Areas that are particularly troublesome are adhesion in the medical field, and attachment of components of very small size, such as in the micro- and nano-techniques. In the medical field, examples of when adhesives have to be used to adhere biological material include repair of lacerated or otherwise damaged organs, especially broken bones and detached retinas and corneas. Dental procedures also often require adhesion of parts to each other, such as during repair of caries, permanent sealants and periodontal surgery. It is very important in biomedical applications of an adhesive and coating composition to use bioacceptable and biodegradable components, which furthermore should not per se or due to contamination induce any inflammation or toxic reactions. In addition, the adhesive has to be able to attach structures to each other in a wet environment. In the electronic industry, a particular problem today is that the components that are to be attached to each other often are of very small size, and the amount of adhesive that is possible to use is very small. Adhesives that provide high adhesive strength even with minor amounts of adhesive are therefore required. Also for non-medical uses, an adhesive that is non-irritating, non-allergenic, non-toxic and environmentally friendly is preferred, in contrast to what many of the adhesives commonly used today usually are.

Polyphenolic proteins, preferentially isolated from mussels, are known to act as adhesives. Examples of such proteins can be found in e.g. U.S. Pat. No. 4,585,585. Their wide use as adhesives has been hampered by problems related to the purification and characterisation of the adhesive proteins in sufficient amounts. Also, mostly when using the polyphenolic proteins as adhesives the pH has had to be raised to neutral or slightly basic (commonly to from 5.5 to 7.5) in order to facilitate oxidation and curing of the protein. However, this curing is slow and results in poor adhesive strength and therefore oxidisers, fillers and cross-linking agents are commonly added to decrease the curing time and obtain a stronger adhesive.

Mussel adhesive protein (MAP) is formed in a gland in the foot of byssus-forming mussels, such as the common blue mussel (*Mytilus edulis*). The molecular weight of MAP from *Mytilis edulis* is about 130.000 Dalton and it has been disclosed to consist of 75-80 closely related repeated peptide sequences. The protein is further characterised by its many epidermal growth factor like repeats. It has an unusual high proportion of hydroxy-containing amino acids such as hydroxyproline, serine, threonine, tyrosin, and the uncommon amino acid 3,4-dihydroxy-L-phenylalanine (Dopa) as well as lysine. It may be isolated either from natural sources or produced biotechnologically. U.S. Pat. No. 5,015,677 as well as U.S. Pat. No. 4,585,585 disclose that MAP has very strong adhesive properties after oxidation and polymerisation, e.g. by the activity of the enzyme tyrosinase, or after treatment with bifunctional reagents.

MAP is previously known to be useful as an adhesive composition e.g. for ophthalmic purposes. Robin et al., Refractive and Corneal Surgery, vol. 5, p. 302-306, and Robin et al., Arch. Ophthalmol., vol. 106, p. 973-977, both disclose MAP-based adhesives comprising an enzyme polymiser. U.S. Pat. No. 5,015,677 also describes a MAP-based adhesive containing a cross-linking agent and optionally a filler substance and a surfactant. Preferred cross-linking agents according to U.S. Pat. No. 5,015,677 are enzymatic oxidising agents, such as catechol oxidase and tyrosinase, but sometimes also chemical cross-linking agents, such as glutaraldehyde and formaldehyde can be used. Examples of fillers are proteins, such as casein, collagen and albumin, and polymers comprising carbohydrate moieties, such as chitosan and hyaluronan. U.S. Pat. No. 5,030,230 also relates to a bioadhesive comprising MAP, mushroom tyrosinase (cross-linker), SDS (sodium dodecyl sulfate, a surfactant) and collagen (filler). The bioadhesive is used to adhere a cornea prosthesis to the eye wall.

EP-A-343 424 describes the use of a mussel adhesive protein to adhere a tissue, cell or another nucleic acid containing sample to a substrate during nucleic acid hybridisation conditions, wherein the mussel adhesive protein, despite the harsh conditions encountered during the hybridisation, provided adherence. US-A-5,817,470 describes the use of mussel adhesive protein to immobilise a ligand to a solid support for enzyme-linked immunoassay. Mussel adhesive protein has also been used in cosmetic compositions to enhance adherence to nails and skin (WO 88/05654).

A major problem associated with known MAP-based bioadhesive compositions, despite the superior properties of MAP per se, is that some constituents, in particular the presently used cross-linking agents, can harm and/or irritate living tissue and cause toxic and immunological reactions. Chemical crosslinking agents, such as glutaraldehyde and formaldehyde, are generally toxic to humans and animals, and it is highly inappropriate to add such agents to a sensitive tissue, such as the eye. Enzymes, such as catechol oxidase and tyrosinase, are proteins, and proteins are generally recognized as potential allergens, especially in case they originate from a species other than the patient. Because of their oxidising and hydrolysing abilities, they can also harm sensitive tissue.

Therefore, there is still a need for new adhesive compositions, both for medical and other applications, that provide strong adhesion with small amounts of adhesive, that are simple to use and that do not cause toxic and allergic reactions.

SUMMARY OF THE INVENTION

The present invention pertains to a method for attaching two surfaces to each other or coating a surface, comprising the steps of providing a bioadhesive composition consisting of a bioadhesive polyphenolic protein derived from a byssus-forming mussel, mixing the bioadhesive protein with a preparation comprising periodate ions, so that the final concentration of periodate ions in the final composition is at least 1.80 ol/g final composition, before applying the composition to the surfaces which are to be attached to each other or the surface to be coated. The surfaces are then joined and left for a sufficiently long time to allow curing to occur or the coated surface is left to cure for a sufficiently long time. The invention can be provided as a kit of parts comprising the bioadhesive protein solution and a preparation of periodate ions. Since the provided compositions are non-toxic and presumably non-allergenic the invention is especially suitable for use in medical applications for adherence or coating of biological tissues. Also, since very strong adhesive strengths are provided using the compositions of the present invention, it is also particularly useful for applications where only minute amounts of adhesives can be used, including non-biological surfaces. The invention can be provided in the form of a kit of parts comprising the MAP-solution and a preparation of periodate ions.

Definitions

As disclosed herein, the terms "polyphenolic protein", "mussel adhesive protein" or "MAP" relates to a bioadhesive protein derived from byssus-forming mussels or which is recombinantly produced. Examples of such mussels are mussels of the genera *Mytilus, Geukensia, Aulacomya, Phragmatopoma, Dreissenia* and *Brachiodontes*. Suitable proteins have been disclosed in a plurality of publications, e.g. U.S. Pat. No. 5,015,677, U.S. Pat. No. 5,242,808, U.S. Pat. No. 4,585,585, U.S. Pat. No. 5,202,236, U.S. Pat. No. 5149,657, U.S. Pat. No. 5,410,023, WO 97/34016, and U.S. Pat. No. 5,574,134, Vreeland et al., J. Physiol., 34: 1-8, and Yu et al., Macromolecules, 31: 4739-4745. They comprise about 30-300 amino acid residues and essentially consist of tandemly linked peptide units comprising 3-15 amino acid residues, optionally separated by a junction sequence of 0-10 amino acids. A characteristic feature of such proteins is a comparatively high amount of positively charged lysine residues, and in particular the unusual amino acid DOPA (L-3,4-dihydroxyphenylalanine). A polyphenolic protein suitable for use in the present invention has an amino acid sequence in which at least 3% and preferably 6-30% of the amino acid residues are DOPA. A few examples of typical peptide units are given below. However, it is important to note that the amino acid sequences of these proteins are variable and that the scope of the present invention is not limited to the exemplified subsequences below, as the skilled person realises that bioadhesive polyphenolic proteins from different sources, including recombinantly produced, can be regarded as equivalent:

a) Val-Gly-Gly-DOPA-Gly-DOPA-Gly-Ala-Lys    SEQ ID NO:1 b) Ala-Lys-Pro-Ser-Tyr-diHyp-Hyp-Thr-DOPA-Lys    SEQ ID NO:2 c) Thr-Gly-DOPA-Gly-Pro-Gly-DOPA-Lys    SEQ ID NO:3 d) Ala-Gly-DOPA-Gly-Gly-Leu-Lys    SEQ ID NO:4 e) Gly-Pro-DOPA-Val-Pro-Asp-Gly-Pro-Tyr-Asp-Lys    SEQ ID NO:5 f) Gly-Lys-Pro-Ser-Pro-DOPA-Asp-Pro-Gly-DOPA-Lys    SEQ ID NO:6 g) Gly-DOPA-Lys    SEQ ID NO:7 h) Thr-Gly-DOPA-Ser-Ala-Gly-DOPA-Lys    SEQ ID NO:8 i) Gln-Thr-Gly-DOPA-Val-Pro-Gly-DOPA-Lys    SEQ ID NO:9 j) Gln-Thr-Gly-DOPA-Asp-Pro-Gly-Tyr-Lys    SEQ ID NO:10 k) Gln-Thr-Gly-DOPA-Leu-Pro-Gly-DOPA-Lys    SEQ ID NO:11

The term "surface" is to be interpreted broadly and may comprise virtually any surface. The choice of surface is not critical to the present invention. Examples of surfaces for which the invention are specially suitable for include non-biological surfaces such as glass, plastic, ceramic and metallic surfaces etc., and biological surfaces, comprising wood and different tissues such as skin, bone, teeth, the eye, cartilage, etc.

By "sufficiently long time" is meant a time period long enough to allow curing of the bioadhesive composition. Curing is often immediate and typically the time period required for curing is from 5 sec to one hour.

By "preparation comprising periodate ions" is meant a non-enzymatic, oxidising preparation comprising periodate ions from any salt comprising such periodate ions, such as $NaIO_4$, $KIO_4$, $RuIO_4$ etc. The preparation can be an aqueous solution comprising the periodate salt or a preparation comprising the solid salt.

DETAILED DESCRIPTION OF THE INVENTION

The object of the present invention is to provide an adhesive composition to be used for attaching two surfaces to each other or coating a surface. The compositions provided in the invention can in principle be used to attach any surfaces to each other or to coat any surface. However, the compositions according to the present invention are particularly useful when adhesive or coating compositions are needed that are non-toxic, non-irritating or non-allergenic, or that can be used in wet environments. Also the compositions of the present invention are useful when a strong adhesion even with small amounts of adhesive, are required. Further advantages with the compositions provided in the present invention are their water solubility, the avoidance of organic solvents commonly used in adhesive or coating compositions, that they are biologically produced and harmless to the environment.

The only mandatory components of the present invention is the polyphenolic protein and periodate ions. Previously when polyphenolic proteins have been used, it has been considered necessary to add additional components, such as fillers and oxidising agents, in order to achieve strong enough adhesive strength and the pH is commonly raised to neutral or slightly basic. The present inventor has shown that a very strong adhesion, comparable to the adhesive strength provided using the commonly used MAP compositions, can be provided simply using a solution of the MAP protein and mixing said MAP protein with preparation of periodate ions so that the concentration of periodate ions in the final composition is at least 1.80 ol/g.

The periodate ions can be provided via a preparation of an aqueous solution comprising any suitable salt comprising such ions, such as $NaIO_4$, $KIO_4$, $RuIO_4$ etc., alone or in different combinations and ratios. Alternatively, the preparation comprising the periodate salt(s) can be dissolved directly in the MAP-solution.

Preferably, the MAP concentration of the present invention is above 10 mg/ml. More preferably the concentration of the MAP-solution is above 20 mg/ml. Typically the concentration is between 20 and 50 mg/ml.

One preferred object of the present invention is to provide an adhesive or coating composition for medical applications, e.g. for attaching biological and/or non-biological components to biological structures, an object for which the MAP protein in itself is well suited, since it is non-toxic and biodegradable. However, the enzymatic oxidising agents commonly added to MAP compositions in order to obtain cross-linking and oxidation can lead to irritation and allergic reactions and those MAP compositions are therefore not optimal for medical applications. Due to the lack of such components in the present invention, the compositions of the present invention are particularly suitable for attachment of biological surfaces to each other or to biological or non-biological components. For the above reasons the compositions of the present invention are also particularly useful for coating of materials used in medical applications or biological tissues.

Due to the very high adhesive strength provided with very small amounts of the compositions of the present invention, one preferred field of application for which the compositions are particularly suitable for attachment of non-biological surfaces such as glass, plastic, ceramic and metallic surfaces. This is particularly useful within the electronic micro- and nano-techniques, optics, etc. for adhesion or coating of, for example, biosensors, microchips, solar cells, mobile phones, etc., since for these applications only minute amounts of adhesive can be used. The compositions of the present invention are also suitable for coating of non-biological surfaces.

The adhesive compositions of the present invention are also useful for attachment of cells, enzymes, antibodies and other biological specimen to surfaces.

According to one aspect of the invention the solution of MAP is mixed with a preparation comprising periodate ions so that the final concentration of periodate ions in the composition is at least 1.80 ol/g final composition. The mixture is then applied to at least one of the surfaces to be attached to each other or to the surface to be coated. Alternatively, the MAP-solution and the preparation comprising periodate ions are separately applied, without any specific order, to at least one of the surfaces, which are to be attached to each other, or a surface to be coated. The MAP-solution can also be applied to one of the surfaces that are to be attached to each other while the preparation comprising periodate ions is applied to the other. If two surfaces are to be attached to each other they are then joined. Finally the attached or coated surfaces are left for a sufficiently long time to allow curing. The time necessary for curing will for example depend on the surfaces attached or coated, and the amount and the composition of the adhesive. Often, however, the curing is immediate and a time period of 5 sec to one hour is typically sufficient for curing to occur.

Preferably the final concentration of periodate ions in the bioadhesive composion according to the present invention is at least 1.90 ol/g final composition, and more preferably at least 2.00 ol/g final composition.

40% by weight of $NaIO_4$ in the final bioadhesive composition equals 1.86 mmol/g in the final composition. However, good adhesive strengths can also be achieved with down to 10% by weight of $NaIO_4$.

The present invention can be provided as a kit of parts useful in a method for attaching surfaces to each other or coating surfaces, comprising the MAP-solution, a solid or liquid preparation comprising the periodate ions and optionally at least one device, such as a syringe, to apply the compositions to the surfaces that are to be attached or coated. Preferred preparations and concentrations of periodate ions, concentration ranges of the MAP-solution, curing times and surfaces to attached or coated for use of this kit are as described above.

EXAMPLE 1

In order to determine the adhesive strength using the compositions of the present invention, the adhesive strength between glass plates and biological tissue (muscle from cattle and pig) was determined. The MAP-solution (in 0.01 M citric acid) from Biopolymer Products of Sweden AB, Alingsas, Sweden) was applied to a glass plate (75×25×2 mm), whereafter the non-enzymatic oxidising agent $NaIO_4$ was applied to the glass plate and carefully mixed with the MAP-solution on the glass plate, before the biological tissue (approximately of the size 40×15×4 mm) was placed on the glass plate and fixed with a clip. The lower amount of $NaIO_4$ (3-6% by weight of final composition, see Table 1-3) was used for comparison. The sample was thereafter allowed to cure under water (35° C.) for 5 min or 1 hour (see Table 1 and 2) or under dry conditions at room temperature for 1 min (see Table 3).

To measure the adhesive strength after curing, the clip was removed from the sample and the sample was attached to a spring balance via the glass plate. The biological tissue was then pulled until it detached from the glass plate and the force needed for this was determined (Table 1-3).

The adhesive area between the glass plate and the biological tissue was ca 0.3-0.4 $cm^2$ on average, but varied from 0.1-0.8 $cm^2$.

As can be seen in Table 1-3, a substantial increase in adhesive strength is obtained, when the very high amount of non-enzymatic oxidising periodate ions according to the present invention, is used.

TABLE 1

Adhesive strength between glass plate and biological tissue
with curing for 5 min under water at 35° C.

| Sample | MAP Concentration (mg/ml) | MAP Amount (μg) | NaIO$_4$ Concentration (M) | NaIO$_4$ Amount (μl) | % NaIO$_4$ in final composition (by weight) | Adhesive strength (g) |
|---|---|---|---|---|---|---|
| 1 | 20 | 60 | 0.01 | 2 | 6 | 90 |
| 2 | 20 | 60 | 0.1 | 2 | 42 | 150 |

TABLE 2

Adhesive strength between glass plate and biological tissue
with curing for 1 hour under water at 35° C.

| Sample | MAP Concentration (mg/ml) | MAP Amount (μg) | NaIO$_4$ Concentration (M) | NaIO$_4$ Amount (μl) | % NaIO$_4$ in final composition (by weight) | Adhesive strength (g) |
|---|---|---|---|---|---|---|
| 1 | 23 | 69 | 0.01 | 2 | 3 | 120 |
| 2 | 24 | 60 | 0.1 | 2 | 42 | 185 |

TABLE 3

Adhesive strength between glass plate and biological tissue with
curing for 1 min under dry conditions at room temperature.

| Sample | MAP Concentration (mg/ml) | MAP Amount (μg) | NaIO$_4$ Concentration (M) | NaIO$_4$ Amount (μl) | % NaIO$_4$ in final composition (by weight) | Adhesive strength (g) |
|---|---|---|---|---|---|---|
| 1 | 24 | 60 | 0.01 | 1.5 | 5 | 25 |
| 2 | 22 | 66 | 0.1 | 3 | 49 | 110 |
| 3 | 24 | 60 | 0.5 | 1.5 | 73 | 125 |
| 4 | 22 | 66 | 0.5 | 3 | 83 | 110 |

EXAMPLE 2

The adhesive strength obtained by employing the compositions of the present invention was compared with the strength obtained by using a common epoxy adhesive.

Two glass plates were attached to each other using either a MAP-solution and a high amount of the non-enzymatic oxidising agent NaIO$_4$. The MAP-solution (in 0.01 M citric acid), from Biopolymer Products of Sweden AB, Alingsas, Sweden) was applied to a glass plate (75×25×2 mm), whereafter the non-enzymatic oxidising agent NaIO$_4$ was applied to the glass plate and carefully mixed with the MAP-solution on the glass plate, before placing a second glass plate onto the first one and fixing the glass plates to each other with a clip. The adhesive area between the glass plates covered was on average 0.5-0.7 cm$^2$ (with a variation from 0.3-1.0 cm$^2$). The samples were allowed to cure at room temperature for 72 hours before determining the shear strength (see Table 4). For comparison the adhesive strength between glass plates by employing common epoxy adhesive (Bostic AB, Helsingborg, Sweden) (10 mg) was determined.

For the determination of shear strength the grip length was 75 and the cross head speed was 3.0 mm/min.

The adhesive strength obtained using the compositions the present invention resulted in very strong adhesive strengths. As a comparison, the adhesive strength obtained employing ca 250 times more of a common epoxy glue is included (see Table 4). Therefore very strong adhesive strengths can be obtained with very small amounts of adhesive when using the compositions of the present invention.

TABLE 4

Adhesive strength between glass plates with curing for
72 hours under dry conditions at room temperature.

| Sample | MAP Concentration (mg/ml) | MAP Amount (μg) | NaIO$_4$ Concentration (M) | NaIO$_4$ Amount (μl) | % NaIO$_4$ in final composition (by weight) | Epoxy glue Amount (mg) | Adhesive strength (N) |
|---|---|---|---|---|---|---|---|
| 1 | 20 | 40 | 0.1 | 1.5 | 44 | — | 141 |
| 2 | 20 | 40 | 0.1 | 1.5 | 44 | — | 119 |
| 3 | — | — | — | — | — | 10 | 380 |

The invention claimed is:

1. A method for coating a surface, comprising:
providing a preparation comprising an aqueous solution of a bioadhesive polyphenolic protein; providing a preparation comprising periodate ions; mixing said bioadhesive composition and said preparation to form an adhesive composition comprising at least 1.80 mmol per gram final composition of periodate ions and wherein the concentration of said polyphenolic protein is said bioadhesive composition is in the range of 10-50 mg/ml final composition; coating the surface with said adhesive composition; and curing said coating, wherein said bioadhesive polyphenolic protein comprises 30-300 amino acids and consists of tandemly linked peptide repeats comprising 3-15 amino acid residues; and at least 6-30% of said 30-300 amino acids are 3,4-dihydroxy-L-phenylalanine (DOPA).

2. A method for coating a surface, comprising:
applying a preparation comprising an aqueous solution of a bioadhesive polyphenolic protein in an amount of 10-50 mq/ml, and a preparation comprising at least 1.80 mmol per gram final composition of periodate ions to the surface; mixing said bioadhesive composition and said preparation to form a coating; and
curing said coating, wherein said bioadhesive polyphenolic protein comprises 30-300 amino acids and consists of tandemly linked peptide repeats comprising 3-15 amino acid residues; and 6-30% of said 30-300 amino acids are 3,4-dihydroxy-L-phenylalanine (DOPA).

3. A method of claim 1 wherein the preparation comprises periodate ions in an amount of at least 1.9 mmol/g final composition of periodate ions.

4. A method of claim 1 wherein the preparation comprises periodate ions in an amount of at least 2.0 mmol/g final composition of periodate ions.

5. The method of claim 1 wherein the surface is a biological surface.

6. The method of claim 1 wherein the surface is a non-biological surface.

* * * * *

SEQUENCE LISTING

<160> NUMBER OF SEQ ID NOS: 11

<210> SEQ ID NO 1
<211> LENGTH: 9
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (4)..(4)
<223> OTHER INFORMATION: DOPA
<220> FEATURE:
<221> NAME/KEY: MISC_FEATURE
<222> LOCATION: (6)..(6)
<223> OTHER INFORMATION: DOPA

<400> SEQUENCE: 1

Val Gly Gly Xaa Gly Xaa Gly Ala Lys
1               5

<210> SEQ ID NO 2
<211> LENGTH: 10
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (6)..(6)
<223> OTHER INFORMATION: diHyp
<220> FEATURE:
<221> NAME/KEY: MISC_FEATURE
<222> LOCATION: (7)..(7)
<223> OTHER INFORMATION: Hyp
<220> FEATURE:
<221> NAME/KEY: MISC_FEATURE
<222> LOCATION: (9)..(9)
<223> OTHER INFORMATION: DOPA

<400> SEQUENCE: 2

Ala Lys Pro Ser Tyr Xaa Xaa Thr Xaa Lys
1               5                   10

<210> SEQ ID NO 3
<211> LENGTH: 8
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (3)..(3)
<223> OTHER INFORMATION: DOPA
<220> FEATURE:
<221> NAME/KEY: MISC_FEATURE
<222> LOCATION: (7)..(7)
<223> OTHER INFORMATION: DOPA

<400> SEQUENCE: 3

Thr Gly Xaa Gly Pro Gly Xaa Lys
1               5

<210> SEQ ID NO 4
<211> LENGTH: 7
<212> TYPE: PRT
<213> ORGANISM: Artificial
<220> FEATURE:

```
<223> OTHER INFORMATION: protein subsequence
<220> FEATURE:
<221> NAME/KEY: MISC_FEATURE
<222> LOCATION: (3)..(3)
<223> OTHER INFORMATION: DOPA

<400> SEQUENCE: 4

Ala Gly Xaa Gly Gly Leu Lys
1               5

<210> SEQ ID NO 5
<211> LENGTH: 11
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (3)..(3)
<223> OTHER INFORMATION: DOPA

<400> SEQUENCE: 5

Gly Pro Xaa Val Pro Asp Gly Pro Tyr Asp Lys
1               5                   10

<210> SEQ ID NO 6
<211> LENGTH: 11
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (6)..(6)
<223> OTHER INFORMATION: DOPA
<220> FEATURE:
<221> NAME/KEY: MISC_FEATURE
<222> LOCATION: (10)..(10)
<223> OTHER INFORMATION: DOPA

<400> SEQUENCE: 6

Gly Lys Pro Ser Pro Xaa Asp Pro Gly Xaa Lys
1               5                   10

<210> SEQ ID NO 7
<211> LENGTH: 3
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (2)..(2)
<223> OTHER INFORMATION: DOPA

<400> SEQUENCE: 7

Gly Xaa Lys
1

<210> SEQ ID NO 8
<211> LENGTH: 8
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (3)..(3)
<223> OTHER INFORMATION: DOPA
```

-continued

```
<220> FEATURE:
<221> NAME/KEY: MISC_FEATURE
<222> LOCATION: (7)..(7)
<223> OTHER INFORMATION: DOPA

<400> SEQUENCE: 8

Thr Gly Xaa Ser Ala Gly Xaa Lys
1               5

<210> SEQ ID NO 9
<211> LENGTH: 9
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (4)..(4)
<223> OTHER INFORMATION: DOPA
<220> FEATURE:
<221> NAME/KEY: MISC_FEATURE
<222> LOCATION: (8)..(8)
<223> OTHER INFORMATION: DOPA

<400> SEQUENCE: 9

Gln Thr Gly Xaa Val Pro Gly Xaa Lys
1               5

<210> SEQ ID NO 10
<211> LENGTH: 9
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (4)..(4)
<223> OTHER INFORMATION: DOPA

<400> SEQUENCE: 10

Gln Thr Gly Xaa Asp Pro Gly Tyr Lys
1               5

<210> SEQ ID NO 11
<211> LENGTH: 9
<212> TYPE: PRT
<213> ORGANISM: Artificial
<220> FEATURE:
<223> OTHER INFORMATION: protein subsequence
<220> FEATURE:
<221> NAME/KEY: MISC_FEATURE
<222> LOCATION: (4)..(4)
<223> OTHER INFORMATION: DOPA
<220> FEATURE:
<221> NAME/KEY: MISC_FEATURE
<222> LOCATION: (8)..(8)
<223> OTHER INFORMATION: DOPA

<400> SEQUENCE: 11

Gln Thr Gly Xaa Leu Pro Gly Xaa Lys
1               5
```